(12) United States Patent
Pompei

(10) Patent No.: US 6,292,685 B1
(45) Date of Patent: Sep. 18, 2001

(54) TEMPORAL ARTERY TEMPERATURE DETECTOR

(75) Inventor: Francesco Pompei, Boston, MA (US)

(73) Assignee: Exergen Corporation, Watertown, MA (US)

(*) Notice: Subject to any disclaimer, the term of this patent is extended or adjusted under 35 U.S.C. 154(b) by 0 days.

(21) Appl. No.: 09/151,482

(22) Filed: Sep. 11, 1998

(51) Int. Cl.[7] .................................................. A61B 6/00
(52) U.S. Cl. ........................ 600/474; 600/475; 600/549; 374/100; 374/104; 374/112; 374/121; 374/123; 374/124; 374/126; 374/129; 374/132; 374/133
(58) Field of Search .................................. 374/124, 121, 374/100, 104, 126, 127, 128, 129, 133; 600/310, 309, 473, 474, 475, 549

(56) References Cited

U.S. PATENT DOCUMENTS

| | | | |
|---|---|---|---|
| 4,302,971 | * 12/1981 | Luk ........................................ | 374/162 |
| 4,428,382 | * 1/1984 | Walsall et al. ........................ | 600/549 |
| 4,494,861 | * 1/1985 | Everest ................................. | 374/124 |
| 4,636,091 | * 1/1987 | Pompei et al. ........................ | 374/124 |
| 4,993,419 | * 2/1991 | Pompei et al. ........................ | 128/664 |
| 5,012,813 | 5/1991 | Pompei et al. ........................ | 128/664 |
| 5,050,612 | * 9/1991 | Matsumura ............................ | 128/670 |
| 5,150,969 | * 9/1992 | Goldberg et al. ..................... | 374/128 |
| 5,187,943 | * 2/1993 | Taniguchi et al. .................... | 62/180 |
| 5,199,436 | 4/1993 | Pompei et al. ........................ | 128/664 |
| 5,271,407 | 12/1993 | Pompei et al. ........................ | 128/664 |
| 5,381,796 | 1/1995 | Pompei .................................. | 128/664 |
| 5,441,476 | * 8/1995 | Kitado et al. .......................... | 600/26 |
| 5,445,158 | 8/1995 | Pompei .................................. | 128/664 |
| 5,653,238 | 8/1997 | Pompei .................................. | 128/664 |
| 5,818,044 | * 10/1998 | Sodickson et al. .................... | 250/339.06 |
| 5,924,996 | * 7/1999 | Cho et al. .............................. | 600/549 |
| 6,059,452 | * 5/2000 | Smith et al. ........................... | 374/169 |

FOREIGN PATENT DOCUMENTS

| | | |
|---|---|---|
| 0 411 121 A1 | 2/1991 | (EP). |
| WO 98/01730 | 1/1998 | (WO). |
| WO 98/08431 | 3/1998 | (WO). |
| WO 99/39166 | 8/1999 | (WO). |

OTHER PUBLICATIONS

U.S. application No. 08/469,484, Pompei et al., filed Apr. 13, 1999.

U.S. application No. 08/738,300, Pompei, filed Feb. 24, 1998.

U.S. application No. 08/881,891, Pompei, filed Mar. 1, 2000.

* cited by examiner

Primary Examiner—Marvin M. Lateef
Assistant Examiner—Jeoyuh Lin
(74) Attorney, Agent, or Firm—Hamilton, Brook, Smith & Reynolds, P.C.

(57) ABSTRACT

Body temperature measurements are obtained by scanning a thermal radiation sensor across the side of the forehead over the temporal artery. A peak temperature measurement is processed to compute an internal temperature of the body as a function of ambient temperature and the sensed surface temperature. The function includes a weighted difference of surface temperature and ambient temperature, the weighting being varied with target temperature through a minimum in the range of 96° F. and 100° F. The radiation sensor views the target surface through an emissivity compensating cup which is spaced from the skin by a circular lip of low thermal conductivity.

37 Claims, 4 Drawing Sheets

TEMPORAL ARTERY TEMPERATURE DETECTOR

BACKGROUND OF THE INVENTION

In recent years, infrared thermometers have come into wide use for detection of temperature of adults. For core temperature readings, infrared thermometers which are adapted to be inserted into the patient's ear have been very successful. Early infrared thermometers were adapted to extend into the ear canal in order to view the tympanic membrane and provide an uncorrected, direct reading of tympanic temperature which correlates with pulmonary artery temperature. More recently, however, to provide for greater comfort and ease of use, ear thermometers have been designed to provide corrected readings of the generally cooler distal ear canal. Such thermometers measure temperature of distal ear canal tissue and calculate arterial core temperature via heat balance.

Core temperature is a term used to describe deep body temperature and is approximated by oral, rectal, ear, pulmonary artery, esophageal and bladder temperatures and the like. Of those temperatures, pulmonary artery temperature is the most precise definition of core temperature since it is closest to the heart and its blood is supplied to all tissues. Calculations of arterial core temperature via heat balance provide approximations of the pulmonary artery temperature, and unless otherwise indicated, core temperature refers to the pulmonary artery temperature.

The arterial heat balance approach is based on a model of heat flow through series thermal resistances from the arterial core temperature to the ear skin temperature and from the ear skin temperature to ambient temperature. Accordingly, after sensing both the skin temperature and ambient temperature, the arterial core temperature can be calculated. The thermal resistance model also allows for computation of equivalent oral and rectal temperatures with the mere adjustment of a weighting factor in the computation. Infrared ear thermometers using the arterial heat balance are disclosed in U.S. Pat. Nos. 4,993,419; 5,012,813; 5,199,436; 5,381,796; 5,445,158; 5,653,238 and 5,271,407, the entire teachings of which are incorporated herein by reference.

To avoid clinical difficulties in using ear thermometers, particularly with neonates, axillary (underarm) infrared thermometers have been introduced. Infrared thermometers designed for axillary temperature measurements are presented in U.S. patent applications Ser. Nos. 08/469,484, 08/738,300 and 08/881,891, the entire teachings of which are incorporated herein by reference. In each of those devices, an infrared detector probe extends from a temperature display housing and may easily slide into the axilla to lightly touch the apex of the axilla and provide an accurate infrared temperature reading in as little as one-half second. The axillary thermometer also relies on the arterial heat balance approach to provide arterial, oral or rectal temperature.

The axillary infrared thermometer has found great utility not only with neonates but as a screening tool in general, and especially for small children where conventional temperature measurements such as a thermometer under the tongue or a rectal thermometer are difficult.

In ear and neonate axillary thermometry, the difference between skin temperature and ambient temperature has been weighted by a coefficient approximating h/pc, where h is an empirically determined coefficient which includes a radiation view factor between the skin tissue and ambient, p is perfusion rate and c is blood specific heat. In ear and neonate axillary thermometry, that coefficient was found empirically to be about 0.09 and 0.05, respectively, with only minor variations. However, with greater exposure for heat transfer and higher vasomotor functions, that coefficient has been determined empirically for the adult axillary region to be about 0.13 with much more significant variations according to the patient's temperature.

SUMMARY OF THE INVENTION

The present invention provides for particularly convenient temperature readings of neonate, child and adult temperatures by detecting the temperature of the forehead directly over the superficial temporal artery.

Because arteries receive blood directly from the heart, they are a good choice for detecting core temperature, but an artery at the extremities of the body, such as those felt as pulse points at the wrist or ankle, are highly subject to vasoconstriction. This means, for example, that when an individual is extremely sick, in shock, or even just cold or nervous, the arteries constrict to reduce the flow of blood to that area as a means of retaining heat, or as in the case of shock, in an effort to redirect the blood to more critical areas of the body. This can result in a large temperature change at the artery which is a local artifact only and not representative of core temperature.

Ruling out those arteries located in the extremities, in attempting to replicate the temperature at the source (the heart), we find, in the temporal artery, an artery as short a distance from the heart as possible, with a high and relatively constant blood flow, and that is readily accessible on all individuals. The heart, the lungs and the brain are vital to our very existence, so the supply of blood is high to these organs and continues as high as possible even through, in the face of grave illness, other areas may shut down to accommodate.

Originating in the heart is the aorta, the main trunk of the arterial system. A direct extension of the aorta is the common carotid artery, a robust artery which runs upward in the neck and divides into the internal and external carotids. But, the carotids, even the external carotid, are at best partially embedded, and at worst completely embedded in the skull, and therefore are not accessible at the skin. Extending directly from the carotid is the temporal artery, again an artery dividing internally and externally. We look to the external branch which travels in front of the ear and up into the soft temple area, terminating in a fork directly between the skin and the skull adjoining the eyebrow.

Demonstrably, the temporal artery is very easily accessible; in fact in most individuals, it is usually quite visible. Terminating in a two-prong fork, it easily doubles the assurance of measuring the correct area. Touching it does not present a risk of injury. There are no mucous membranes present, thus eliminating the risk of contaminates such as those found in the mouth and rectum. And, despite lying so close to the skin surface, the temporal artery perfusion, which is the flow of blood per unit volume of tissue, remains relatively constant and so ensures the stability of blood flow required for our measurement.

In accordance with one aspect of the invention, a temperature sensor is scanned across the forehead, preferably in the vicinity of the temporal artery, and a peak temperature reading is provided from the scan. At least three readings per second should be made during the scan, preferably about ten readings per second. The method can be extended to other arteries near the skin such as in the axilla. The preferred radiation sensor is a radiation sensor which views a target surface of the forehead through a reflective cup. The cup has a large open diameter close to the target surface and a window at the base of the cup through which the radiation sensor views the target, the cup being out of the field of view of the sensor. The reflective cup is spaced from the target surface by a smooth lip of low thermal conductivity material.

As in prior ear and axillary thermometers, internal core temperature can be computed from the function $$T_c = (1 + (h/pc))(T_s - T_a) + T_a \qquad (1)$$

where $T_s$ and $T_a$ are the skin and ambient temperatures. The function can be seen to include a weighted difference of surface temperature and ambient temperature with a weighting coefficient h/pc.

In accordance with another aspect of the invention, electronics in the detector compute an internal temperature of the body as a function of ambient temperature and sensed surface temperature. The function includes a weighted difference of surface temperature and ambient temperature, the weighting being varied with target temperature. The weighting varies with target temperature through a minimum in the range of 96° F. to 1 00° F., the weighting increasing above and below the minimum. In particular, the weighting is an approximation of h/pc at the forehead artery where h is a heat transfer coefficient between the target surface and ambient, p is perfusion rate and c is blood specific heat. In a preferred embodiment, the weighting is a linear approximation having a minimum between 96° F. and 97° F. The approximation of h/pc at the minimum is about 0.19. In another embodiment, the weighting includes a polynomial approximation of $1 + h/pc = k_1 T_s^2 - k_2 T_s + k_3$ where h is a heat transfer coefficient between the target surface and ambient, p is perfusion rate, c is blood specific heat, $T_s$ is skin temperature, $k_1$ is approximately 0.00359, $k_2$ is approximately 0.708 and $k_3$ is approximately 36.1.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
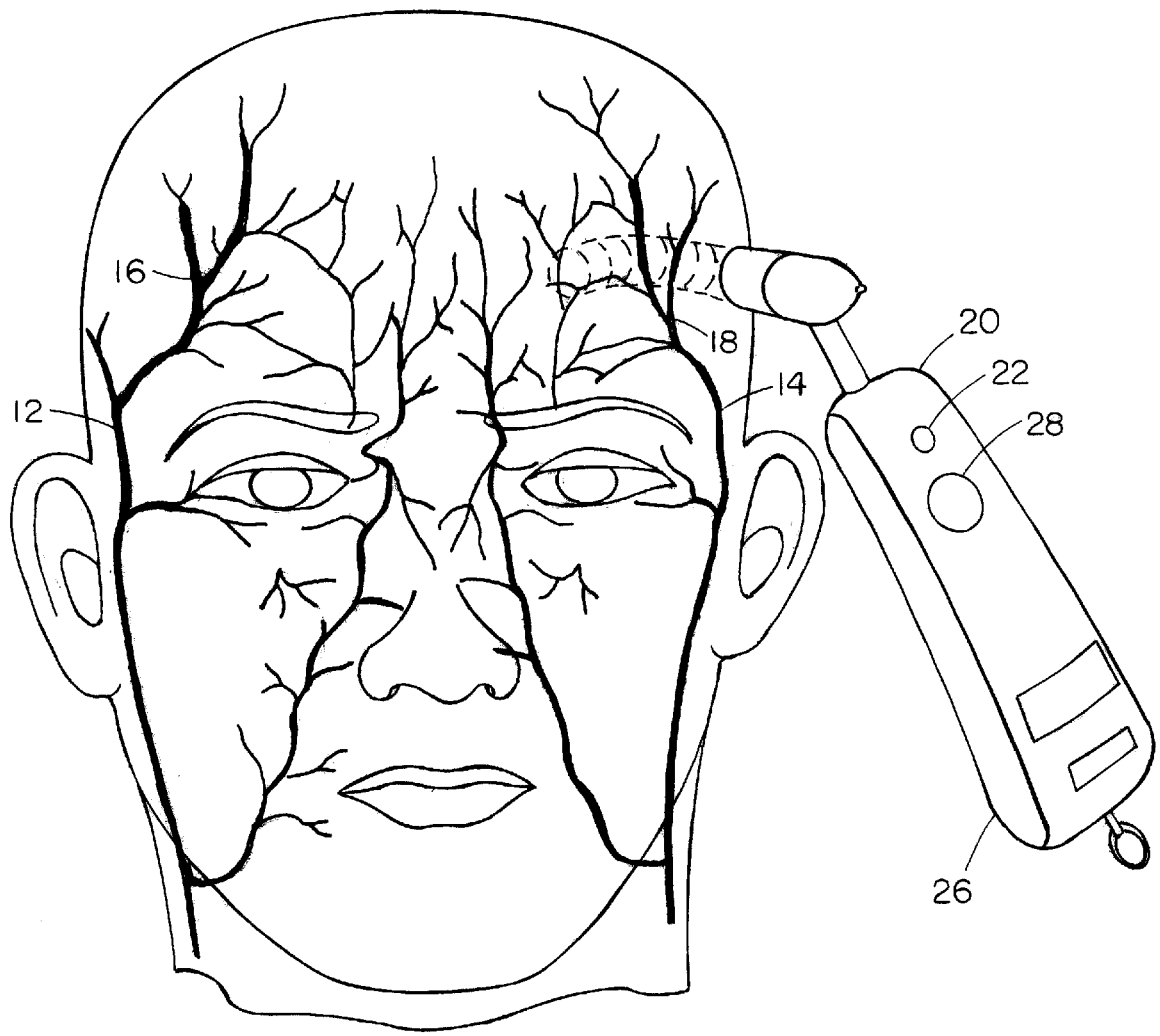
FIG. 1 illustrates an infrared thermometer scanning the temporal artery in the forehead in accordance with the present invention.

As illustrated in FIG. 1, the temporal arteries 12 and 14 extend upwardly toward the side of the human face and bifurcate at 16 and 18 in the forehead region. In that region, the temporal artery passes over the skull bone very close to the skin and is thus termed the superficial temporal artery. The superficial temporal artery is, therefore, particularly accessible for providing temperature readings and, as an artery, has a temperature close to the heart temperature. Further, there are no known arterial/venus anastomoses, that is, shunts between the artery and veins for regulation of skin temperature. Accordingly, the blood flow is relatively stable, varying a maximum of only 50% as opposed to as much as 500% in other areas of the skin.

To locate the temporal artery, a temperature sensor, preferably a radiation detector 20, is scanned across the side of the forehead over the temporal artery while electronics in the detector search for the peak reading which indicates the temporal artery. Preferably, that temperature reading is then further processed in accordance with an algorithm specific to the temporal artery for providing a display temperature which may, for example, correspond to core, oral or rectal temperature.

The temperature detector 20 provides an audible beep with each peak reading. A display 26 provides the temperature reading resulting from the electronic processing discussed below, updated to each new peak reading. A button 28 enables the user to activate the temperature detector. In one embodiment, an LED 22 which flashes with each peak reading can be observed when someone other than the patient performs the reading, and another LED on the other side of the housing can be observed by the patient, particularly when taking his own temperature.

Figure 2A:
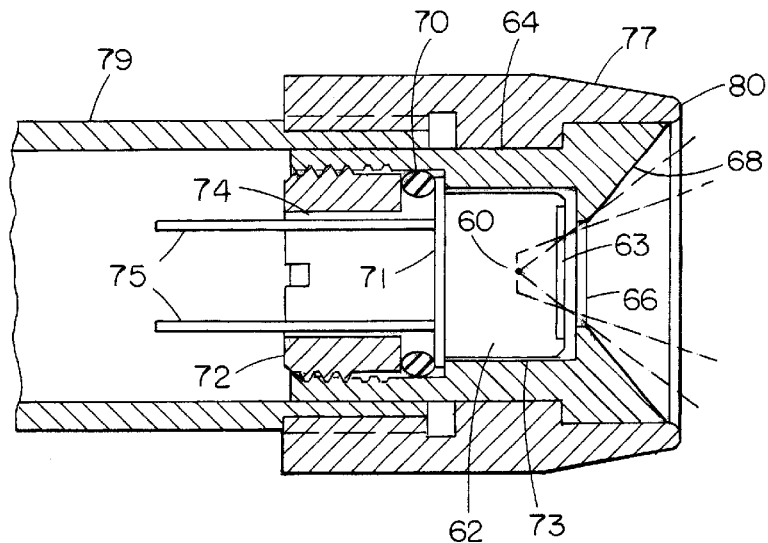
FIGS. 2A, B and C are cross-sectional views of three embodiments of the radiation sensor assembly of the invention.

FIG. 2A illustrates one sensor assembly for the radiation detector of FIG. 1. The assembly is similar to that presented in application Ser. No. 08/881,891. A thermopile 60 is mounted within a can 62 in conventional fashion. For high stability the thermopile may be a vapor deposited thermopile surrounded with xenon gas, but for reduced cost it may be a semiconductor thermopile surrounded with air. An infrared radiation transparent window 63 is provided over a viewing opening in the can. The can 62 is set within a bore within a heat sink 64. A shoulder defines an aperture 66 at the base of a conical cup 68 through which the thermopile views the target. The cup is preferably of low emissivity in order to provide emissivity compensation as disclosed in U.S. Pat. No. 4,636,091. Preferably, the heat sink 64 in which the cup is formed is of aluminum. Alternatively, the heat sink may be of brass, nickel plated in the cup region.

An elastomeric o-ring 70 is positioned behind the can 62. A plug 72 is threaded into the bore in the heat sink 64 to press the ring 70 against the rear flange 71 of the can and thus press the flange against a shoulder in the heat sink bore. With the flange pressed against the shoulder and having a close tolerance with the larger diameter of the bore, an air gap 73 is maintained about the side and front of the can. This arrangement provides for good thermal contact between the can and the heat sink 64 at the rear and also makes the thermopile highly resistant to mechanical shock since the shock is only transferred through the thin flange past the shock absorbing elastomer. If the flange were rigidly clamped between metal parts, there would be a danger of shock breaking the gas seal of the can. An opening 74 is provided through the center of the plug 72 for access of electrical leads 75 to the thermopile can. The heat sink 64 is press fit in a plastic cap 77 which is threaded on to the tubular head 79 of the detector.

The plastic cap 77 in which the sensor assembly is mounted is of low thermal conductivity, preferably less than one hundredth that of aluminum. The housing thermally isolates the heat sink 64 from the surrounding environment to minimize heat flow to the heat sink. Further, the heat sink 64 is of significant thermal mass. Accordingly, the RC time constant for change in temperature of the radiation sensor, with change in temperature to which the housing is exposed, can be made large for a more stable temperature reading. The thermal resistance is made high by the low conductivity housing, and the thermal capacitance is made high by the large mass of the heat sink 64. That RC time constant should be at least 5 minutes and is preferably about 25 minutes.

Past designs of infrared thermometers, such as presented in U.S. Pat. No. 4,993,419, have relied on a massive thermopile can which also served as the heat sink. That design assured a high RC time constant for thermal conduction through the external thermal barrier to the heat sink relative to a thermal RC time constant for temperature response of the cold junction to heat transferred to the heat sink. The latter low RC time constant was obtained by assuring a low thermal resistance to the cold junction using expensive high conductivity material in a specially designed can/heat sink. In the present device, a design goal is to use a conventional low cost thermopile mounted in a light weight can which does not provide the low thermal resistance of the prior design. Accordingly, it is important that the can be mounted to assure that all heat conduction to the thermopile be through the rear of the can which serves as the thermal ground to the thermopile. That objective is obtained by making thermal contact to the can through the rear flange and assuring an air space about the sides and front of the can.

Forming the emissivity compensating cup 68 in the heat sink reduces the cost of the assembly and also improves the thermal characteristics. Although the emissivity of the cup is ideally zero, it is in fact about 0.1. With the cup formed as part of the heat sink, it is at the temperature to which the can is grounded. Accordingly, any thermal emissions from the surface 68 will be at substantially the same temperature as the cold junction and thus not be seen. The electronics can also be calibrated to compensate for the loss of reflectance due to non-ideal emissivity, but that calibration is affected by the temperature of the reflective surface. By assuring that the surface 68 is at the temperature to which the thermopile can is grounded, the temperature of the surface is generally known and compensation can be made temperature dependent.

When adapted to household use, concerns for patient cross-contamination associated with clinical temperature detectors is not so significant. Further, at the forehead, evaporation of moisture is not as significant as in the ear and axillary applications. Accordingly, the disposable radiation transparent covers used in prior infrared thermometers, such as in Ser. Nos. 08/469,484 and 08/738,300 is less desirable. However, in the clinical environment, the transparent cover is still preferred to prevent cross contamination.

During the scanning of the radiation detector across the forehead, contact of the housing 78 with the skin can cause cooling of the skin. To minimize that cooling, a circular lip 80 protrudes axially beyond the tip of the heat sink 64. The lip has a thin radius of 0.02 to 0.05 inch, preferably about 0.03 inch, to minimize the thermal conductance through the insulation material. The heat sink 64 is recessed 0.02 to 0.05 inch, preferably about 0.03 inch, behind the tip of the lip. For comfort during scanning, the lip has a smooth curve.

Figure 2B:
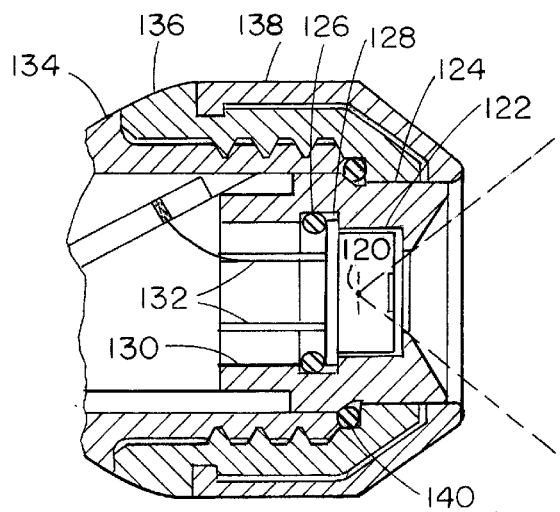

Another embodiment of the radiation sensor assembly is presented in FIG. 2B. As in the prior embodiment, the thermopile 120 is positioned within a can 122. The can is retained in a heat sink 124 by an o-ring 126 which presses against the flange 128 of the can and is set within a circumferential groove in the bore 130 of the heat sink. As before, wires 132 extend through that bore. The housing 134 of the detector head is a split tube formed of two parts which meet along longitudinal seams. The two tube parts are held together by a nut 136 to which a plastic cap 138 is snap fit. The heat sink is retained in the assembly by an o-ring 140 which is seated within a groove in the heat sink and a groove in the nut 136. As before, the cap 138 has a curved lip which extends beyond the tip of the heat sink 124. Cap 138 is of soft material for the comfort of the patient.

Figure 2C:
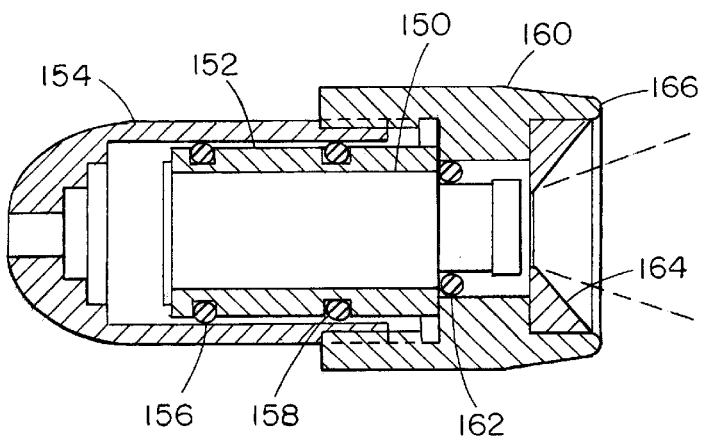

In the embodiment of FIG. 2C, the thermopile is positioned within a can 150 of high thermal mass similar to that disclosed in U.S. Pat. 5,012,813. The can is set within a sleeve 152 which is retained in the head housing 154 by o-rings 156 and 158. A plastic cap 160 is threaded onto the head 154, and the can 150 is centered within the cap by an additional o-ring 162. A low emissivity cup 164 is press fit within the cap 160 and, as before, is recessed behind a smooth lip 166.

Figure 3:
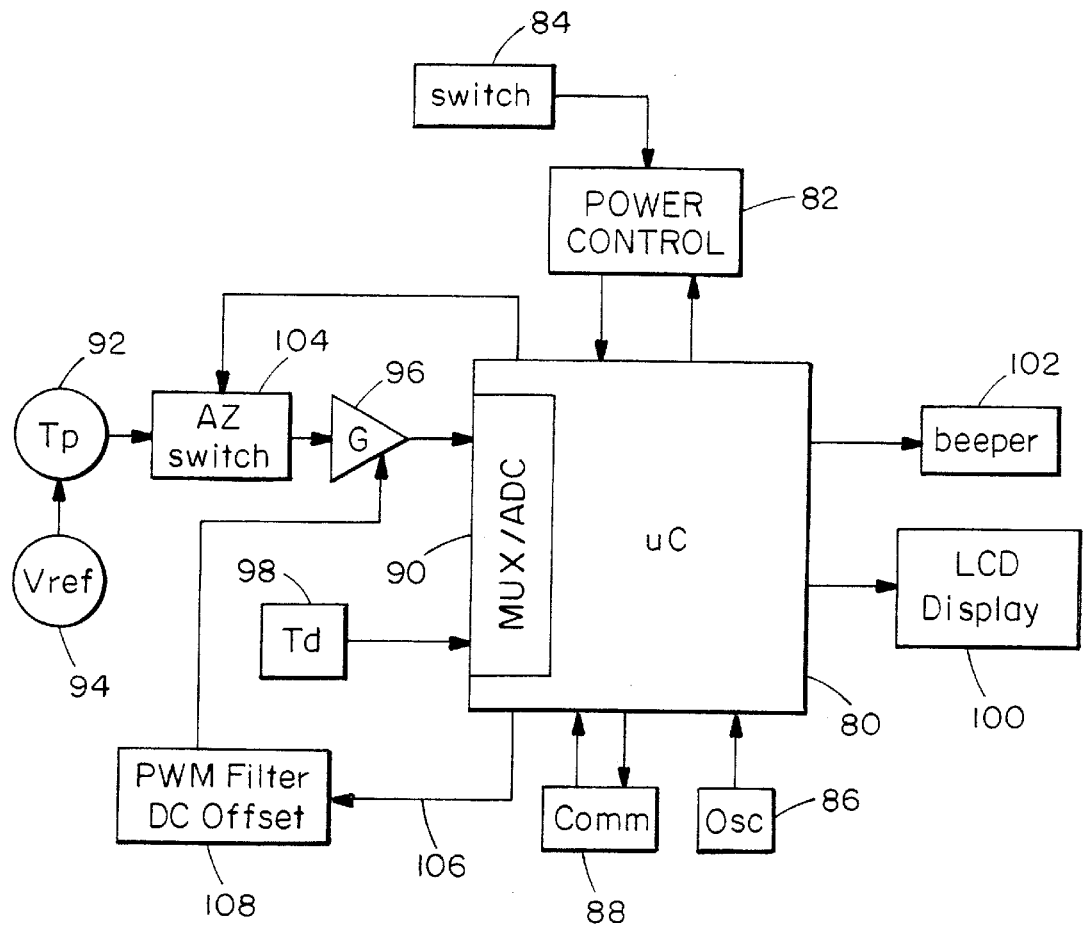
FIG. 3 is an electrical block diagram of the electronics of the thermometer of FIG. 1.

An electrical block diagram for the radiation detector is presented in FIG. 3. A microprocessor 80 is at the heart of the circuit. A power control circuit 82 responds to activation of the button switch 84 by the user to apply power to the microprocessor and other elements of the circuit. That power is maintained until the microprocessor completes the measurement cycle and signals the power control 82 to power down. The microprocessor is clocked by an oscillator circuit 86 and may communicate with an external source for programming and calibration through communication conductors 88. The temperature determined by the microprocessor is displayed on the liquid crystal display 100, and detection of peaks during the temperature processing is indicated by a beeper 102. Peaks are detected from readings taken at least three times per second, and preferably about ten times per second, for rapid scan across the forehead to avoid cooling of the forehead through the detector. During the measurement process, the microprocessor takes readings through a multiplexer/analog-to-digital converter 90. The preferred microprocessor 80 is a PIC16C74 which includes an internal 8-bit A-D converter. To minimize expense, the circuit is designed to rely solely on that A-D converter.

Thermopile 92 provides a voltage output signal equal to the fourth power difference between target temperature and the temperature of the thermopile cold junction, offset by voltage reference 94. The voltage output from the thermopile is amplified by an amplifier 96, having a gain in the order of 1000, which also provides an offset determined by a pulse width modulated filter 108 controlled by the microprocessor. Through operation of the multiplexer, the microprocessor provides an analog-to-digital conversion of the amplified sensor output and of the detector temperature $T_d$ provided by temperature sensor 98. The temperature sensor 98 is positioned to sense the substantially uniform temperature of the thermopile cold junction, can and heat sink. An auto zero switch 104 is included to allow for isolation of the amplifier 96 from the thermopile 92 during a calibration sequence as discussed in prior U.S. application Ser. No. 08/738,300.

It is well known that the output of the thermopile is proportional to $(T_s^4 - T_d^4)$ where $T_s$ is the target skin temperature viewed by the radiation detector and $T_d$ is the temperature of the detector measured by sensor 98. From that relationship, $T_s$ can be computed. It is also known that, based on the determined skin temperature and the ambient temperature to which the skin is exposed, an internal core temperature can be computed using the arterial heat balance approach illustrated in FIG. 4. Heat flux q from the internal core temperature $T_c$ passes through the skin 30 to the ambient environment at temperature $T_a$. The skin is thus held at some intermediate temperature $T_s$.

The heat loss of skin, such as at the forehead, the external ear canal or axilla, to the environment can be calculated with the following well-known equation:

$$q=hA(T_s-T_a) \quad (2)$$

where q is heat flow, A is surface area, $T_s$ and $T_a$ the skin and ambient temperatures, respectively, and h is an empirically determined coefficient which includes a radiation view factor between the skin tissue and ambient. The equation takes the linear form for simplicity. Although the exact form of the equation is fourth-power due to the radiation exchange, the linearized form provides excellent accuracy over the range of interest of about 90° to 105° F.

Heat flow from the core arterial source to the skin is via blood circulation, which is many times more effective than tissue conduction. Thermal transport via the circulation can be described with the following equation:

$$q=wc(T_c-T_s) \quad (3)$$

where q again is heat flow, w is blood mass flow rate, c is blood specific heat, and $T_c$ and $T_s$ are core and skin temperatures, respectively.

Accordingly, the skin can be viewed thermally as tissue being warmed by its blood supply as governed by equation 3, balanced by radiating heat to ambient as governed by equation 2.

Equating:

$$hA(T_s-T_a)=wc(T_c-T_s) \quad (4)$$

Simplifying by dividing by surface area A:

$$h(T_s-T_a)=pc(T_c-T_s) \quad (5)$$

where p is blood flow per unit area, also termed perfusion rate.

Equation 5 then provides a method to calculate core temperature $T_c$ when skin temperature $T_s$ and ambient temperature $T_a$ are known, and the coefficients (or their ratio) have been empirically determined.

Solving for $T_c$:

$$T_c=(h/pc)(T_s-T_a)+T_s \quad (6)$$

where h/pc, the weighting coefficient which weights the difference of surface temperature and ambient temperature, is empirically determined on a statistical basis over a range of patients and clinical situations.

An alternative method of calculating is to employ an electrical analog technique, since equations 2 and 3 have the identical form of a simple voltage/current relationship. The method employs the convention that electrical current is analogous to heat flow and voltage differential is analogous to temperature differential.

Figure 4:
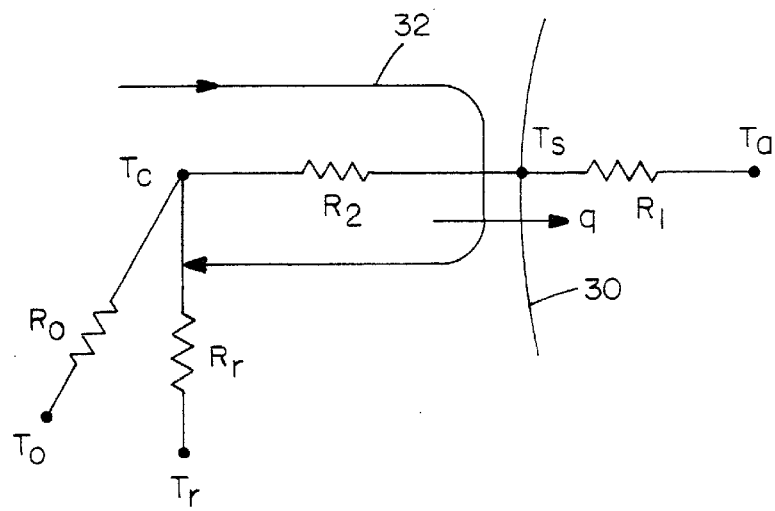
FIG. 4 illustrates the arterial heat balance model.

Accordingly, equations 2 and 3 may be written as:

$$q=(1/R_1)(T_s-T_a) \quad (7)$$

$$q=(1/R_2)(T_c-T_s) \quad (8)$$

and the electrical circuit can be drawn, with $T_c$ and $T_a$ as constant temperature (voltage) reservoirs (FIG. 4). A third equation with a more convenient form can be written as:

$$q=(1/(R_1+R_2))(T_c-T_a) \quad (9)$$

Using equations 7 and 9 and solving for $T_c$:

$$T_c=((R_1+R_2)/R_1)(T_s-T_a)+T_a \quad (10)$$

and finally:

$$T_c=k(T_s-T_a)+T_a \quad (11)$$

which is the precise form of the heat balance equation programmed into arterial heat balance instruments, with $(R_1+R_2)/R_1$ expressed as the k-Factor.

The k Factor can be rewritten as follows:

$$k = \frac{R_1 + R_2}{R_1} = 1 + \frac{R_2}{R_1} = 1 + (h/pc) \quad (12)$$

Accordingly, in either form, equation 6 or 11, it can be seen that the weighting coefficient h/pc is applied to the difference of surface and ambient temperature.

In the weighting coefficient, c is a constant. In ear temperature and neonatal axillary temperature measurements, the perfusion rate is also generally constant, resulting in h/pc of about 0.09 for adult ears and 0.05 for neonates. For a normal adult, the perfusion rate of the axilla is such that the weighting coefficient h/pc is about 0.13. Further, the perfusion rate varies according to the condition of the patient. In particular, with a fever, the perfusion rate can become much higher. Similarly, in the forehead, perfusion rate varies with skin temperature.

Figure 5:
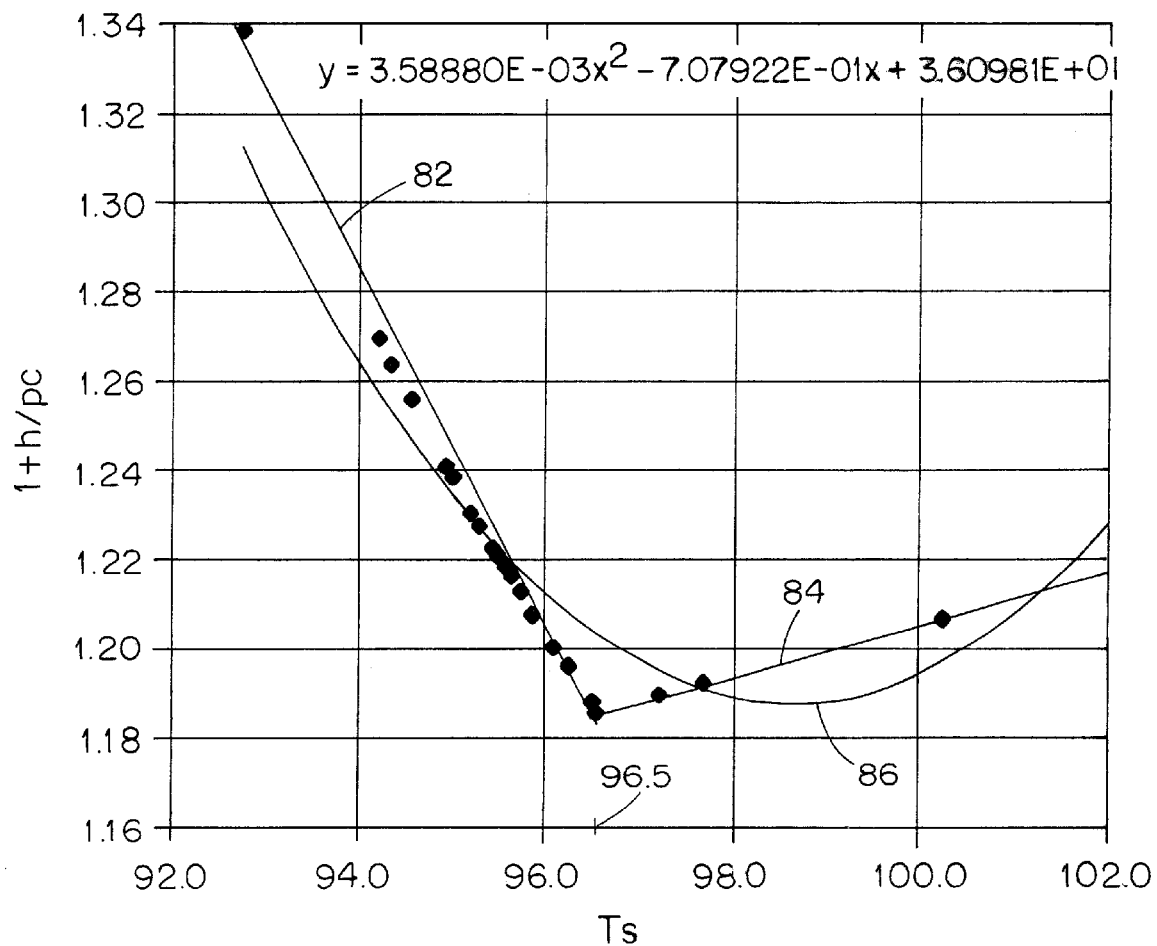
FIG. 5 illustrates the change in weighting coefficient (1+h/pc) with change in skin temperature.

In both the ear and axilla, the coefficient h is relatively constant. The forehead has greater exposure to the ambient environment, and the radiation heat loss increases with increased skin temperature. Thus, where the weighting coefficient h/pc decreased for all increasing skin temperatures in the ear and axilla temperature measurements, it has been found that, as illustrated in FIG. 5, the weighting coefficient reaches a minimum at near normal body temperature and then, due to the increasing value of h, increases. Empirical data suggests that the value h/pc decreases linearly 82 to a value of about 0.19 and a temperature of about 96–97° F. The coefficient then increases linearly with skin temperature but at a lesser slope at 84. The linear approximations illustrated in FIG. 5 are used in the computations in the clinical model. However, in the consumer model, those linear approximations are replaced by a single polynomial approximation 86:

$$1+h/pc=0.0035888T_s^2-0.707922T_s+36.0981$$

Since all body site temperatures of interest arise from the arterial temperature source, the arterial heat balance can be applied to any site. Accordingly, based on the Thevenin equivalents theorem, oral and rectal diagnostic equivalents $T_o$ and $T_r$ of arterial temperature can be calculated by appropriate selection of k-Factor, empirically taking into consideration resistances $R_0$ and $R_r$.

Individual aspects of the radiation detector which make it particularly suited to providing temperature readings from the temporal artery and other arteries can be found in applicant's prior designs. However, none of those designs provide the unique combination of elements which enable consistent measurements of core temperature by scanning across a superficial artery. Specifically, the Exergen D501 Industrial Temperature Detector used in emissivity compensating cup and provided a peak temperature based on about ten temperature readings per second. However, that device did not perform a heat balance computation and was thus not suited to measurement of core temperature. The emissivity compensating cup was utilized in the axillary temperature detector with a heat balance computation, but that unit was not adapted to be scanned across the target surface. The detected peak in that device used to indicate when the reading had stabilized and could be relied upon. That peak detection was based on only one reading per second. Applicant's prior ear temperature detectors have obtained a peak temperature from ten readings per second but with pivoting of the detector rather than with lateral scan across the target surface. There was no emissivity compensating cup.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of detecting human body temperature comprising:
   laterally scanning a temperature detector across a forehead; and
   providing a peak temperature reading from plural readings during the step of scanning.

2. A method as claimed in claim 1 wherein the temperature detector comprises a radiation sensor which views a target surface area of the forehead.

3. A method as claimed in claim 2 wherein the radiation sensor views the target surface area through a reflective cup, the cup having a large open diameter close to the target surface area and a window at the base of the cup through which the radiation sensor views the target surface area, the cup being out of the field of view of the sensor.

4. A method as claimed in claim 1 further comprising computing an internal body temperature as a function of ambient temperature and the peak temperature reading.

5. A method as claimed in claim 4 wherein the function includes a weighted difference of surface temperature and ambient temperature, the weighting including an approximation of h/pc at a forehead artery where h is a heat transfer coefficient between a target surface of the forehead and ambient, p is perfusion rate and c is blood specific heat.

6. A method as claimed in claim 5 wherein the approximation of h/pc at the minimum is about 0.19.

7. A method as claimed in claim 4 wherein the temperature detector comprises a radiation sensor which views a target surface area of the forehead.

8. A method as claimed in claim 7 wherein the radiation sensor views the target surface area through a reflective cup, the cup having a large open diameter close to the target surface area and a window at the base of the cup through which the radiation sensor views the target surface area, the cup being out of the field of view of the sensor.

9. A method as claimed in claim 8 wherein the reflective cup is spaced from the target surface area by a smooth lip of low thermal conductivity material.

10. A method as claimed in claim 4 wherein the weighting is a linear approximation having a minimum between 96° F. and 97° F.

11. A method as claimed in claim 4 wherein the weighting includes a polynomial approximation of $1+h/pc=k_1 T_s^2 - k_2 T_s + k_3$ where h is a heat transfer coefficient between the target surface and ambient, p is perfusion rate, c is blood specific heat, $k_1$ is approximately 0.00359, $k_2$ is approximately 0.708 and $k_3$ is approximately 36.1.

12. A method as claimed in claim 1 wherein the temperature detector is scanned across an artery.

13. A method as claimed in claim 1 wherein the temperature detector is scanned across a temporal artery.

14. A method of detecting human body temperature comprising:
   detecting temperature at a forehead through a lateral scan across the temporal artery; and
   computing an internal body temperature of the body as a function of ambient temperature and sensed surface temperature.

15. A method as claimed in claim 14 wherein the function includes a weighted difference of surface temperature and ambient temperature, the weighting being varied with target temperature through a minimum in the range of 96° F.–100° F., the weighting increasing above and below the minimum.

16. A method as claimed in claim 14 wherein the function includes a weighted difference of surface temperature and ambient temperature, the weighting including an approximation of h/pc at a forehead artery where h is a heat transfer coefficient between the target surface and ambient, p is perfusion rate and c is blood specific heat.

17. A method as claimed in claim 14 wherein the temperature detector comprises a radiation sensor which views a target surface area of the forehead.

18. A method as claimed in claim 17 wherein the radiation sensor views the target surface area through a reflective cup, the cup having a large open diameter close to the target surface area and a window at the base of the cup through which the radiation sensor views the target surface area, the cup being out of the field of view of the sensor.

19. A method as claimed in claim 18 wherein the reflective cup is spaced from the target surface area by a smooth lip of low thermal conductivity material.

20. A method as claimed in claim 14 wherein temperature is detected in the vicinity of an artery.

21. A method as claimed in claim 14 wherein temperature is detected in the vicinity of a temporal artery.

22. A method of detecting human body temperature comprising:
   laterally scanning a temperature detector across an artery; and
   providing a peak temperature reading from plural readings during the step of scanning.

23. A method as claimed in claim 22 wherein the temperature detector comprises a radiation sensor which views a target surface area over the artery.

24. A method as claimed in claim 23 wherein the radiation sensor views the target surface area through a reflective cup, the cup having a large open diameter close to the target surface area and a window at the base of the cup through which the radiation sensor views the target surface area, the cup being out of the field of view of the sensor.

25. A method as claimed in claim 22 further comprising computing an internal temperature of the body as a function of ambient temperature and sensed surface temperature, the function including a weighted difference of surface temperature and ambient temperature, the weighting being varied with target temperature through a minimum in the range of 96° F. to 100° F., the weighting increasing above and below the minimum.

26. A method as claimed in claim 22 wherein the temperature detector is scanned across a temporal artery.

27. A method of detecting human body temperature comprising measuring temperature of the temporal artery through skin.

28. A method as claimed in claim 27 wherein temporal artery temperature is measured with an infrared detector.

29. A method as claimed in claim 28 wherein the infrared detector is scanned across the temporal artery.

30. A method as claimed in claim 27 further comprising computing an internal temperature of the body as a function of ambient temperature and sensed surface temperature.

31. A method as claimed in claim 30 wherein the function includes a weighted difference of surface temperature and ambient temperature, the weighting including an approximation of h/pc at a forehead artery where h is a heat transfer coefficient between the target surface and ambient, p is perfusion rate and c is blood specific heat.

32. A method of detecting human body temperature comprising:

detecting temperature at a forehead; and computing an internal body temperature of the body as a function of ambient temperature and sensed surface temperature, the function including a weighted difference of surface temperature and ambient temperature, the weighting including an approximation of h/pc at a forehead artery where h is a heat transfer coefficient between the target surface and ambient, p is perfusion rate and c is blood specific heat.

33. A body temperature detector system comprising:

a temperature detector; and electronic circuitry which measures peak temperature from at least three readings per second during scan of the temperature detector across an artery and which processes the measured peak temperature to provide a temperature display based on a model of heat balance relative to a detected arterial temperature, the electronic circuitry computing an internal temperature of the body as a function of ambient temperature and sensed surface temperature, the function including a weighted difference of surface temperature and ambient temperature, the weighting including an approximation of h/pc at a forehead artery where h is a heat transfer coefficient between the target surface and ambient, p is perfusion rate and c is blood specific heat.

34. A detector system as claimed in claim 33 wherein the approximation of h/pc at the minimum is about 0.19.

35. A body temperature detector system comprising:

a temperature detector; and electronic circuitry which measures peak temperature from at least three readings per second during scan of the temperature detector across an artery and which processes the measured peak temperature to provide a temperature display based on a model of heat balance relative to a detected arterial temperature, the electronic circuitry computing an internal temperature of the body as a function of ambient temperature and sensed surface temperature, the function including a weighted difference of surface temperature and ambient temperature, the weighting being a linear approximation having a minimum between 96° F. and 97° F.

36. A body temperature detector system comprising:

a temperature detector; and electronic circuitry which measures peak temperature from at least three readings per second during scan of the temperature detector across an artery and which processes the measured peak temperature to provide a temperature display based on a model of heat balance relative to a detected arterial temperature, the electronic circuitry computing an internal temperature of the body as a function of ambient temperature and sensed surface temperature, the function including a weighted difference of surface temperature and ambient temperature, the weighting including a polynomial approximation of $1+h/pc=k_1T_s^2-k_2T_s+k_3$ where h is a heat transfer coefficient between the target surface and ambient, p is perfusion rate, c is blood specific heat, $k_1$ is approximately 0.00359, $k_2$ is approximately 0.708 and $k_3$ is approximately 36.1.

37. A body temperature detection system comprising:

a temperature sensor which senses temperature of a skin surface; and electronic circuitry which computes an internal temperature of the body as a function of ambient temperature and sensed surface temperature, the function including a weighted difference of surface temperature and ambient temperature, the weighting being varied with target temperature through a minimum in the range of 96° F.–100° F., the weighting increasing above and below the minimum, the weighting including an approximation of h/pc at a forehead artery where h is a heat transfer coefficient between the target surface and ambient, p is perfusion rate and c is blood specific heat, the approximation of h/pc at the minimum being about 0.19.

* * * * *